United States Patent
Merical et al.

(10) Patent No.: US 8,003,179 B2
(45) Date of Patent: Aug. 23, 2011

(54) FILMS HAVING A DESICCANT MATERIAL INCORPORATED THEREIN AND METHODS OF USE AND MANUFACTURE

(75) Inventors: Rick Merical, Appleton, WI (US); Lee Murray, Appleton, WI (US); James Sikorsky, Appleton, WI (US)

(73) Assignee: Alcan Packaging Flexible France, Paris (FR)

( * ) Notice: Subject to any disclaimer, the term of this patent is extended or adjusted under 35 U.S.C. 154(b) by 59 days.

(21) Appl. No.: 11/461,680

(22) Filed: Aug. 1, 2006

(65) Prior Publication Data

US 2007/0160789 A1      Jul. 12, 2007

Related U.S. Application Data

(63) Continuation-in-part of application No. 11/401,633, filed on Apr. 11, 2006, now abandoned, which is a continuation-in-part of application No. 10/385,131, filed on Mar. 10, 2003, now abandoned, which is a continuation-in-part of application No. 10/175,662, filed on Jun. 20, 2002.

(51) Int. Cl.
*B32B 27/18* (2006.01)
*B32B 27/08* (2006.01)
*A61B 17/3215* (2006.01)

(52) U.S. Cl. ............ 428/35.9; 428/35.2; 428/35.5; 428/35.7; 206/363

(58) Field of Classification Search ............ 428/35.7, 428/35.2, 35.3, 35.8, 35.9, 458, 461, 469, 428/475.5, 476.1, 483, 515, 35.4; 206/204, 206/363; 53/400, 425, 434
See application file for complete search history.

(56) References Cited

U.S. PATENT DOCUMENTS

| | | | |
|---|---|---|---|
| 2,987,174 A | 6/1961 | Free et al. |
| 3,063,767 A | 11/1962 | Heuer |
| 3,326,810 A | 6/1967 | Dolan et al. |
| 3,704,806 A | 12/1972 | Plachenov et al. |
| 3,804,663 A | 4/1974 | Clark |
| 3,809,223 A | 5/1974 | Kendall |

(Continued)

FOREIGN PATENT DOCUMENTS

EP    0 454 967 B1    12/1995

(Continued)

OTHER PUBLICATIONS

International Preliminary Report on Patentability in related International Patent Application No. PCT/US2007/066456, dated Jul. 31, 2008.

(Continued)

*Primary Examiner* — Mark Ruthkosky
*Assistant Examiner* — Erik Kashnikow
(74) *Attorney, Agent, or Firm* — RatnerPrestia

(57) ABSTRACT

Film structures, packages, films and methods of making the same are provided wherein the film structures have a desiccant material incorporated into at least one layer of the film structures and further wherein the film structures can comprise a material for making a peelable seal when the film structures are heat sealed to other film structures. The film structures are utilized for a package to hold a product that may be sensitive to the presence of moisture. The product may preferably be pharmaceutical products, nutraceutical products, or devices such as absorbable sutures or medical stents, although any moisture-sensitive product is contemplated by the present invention.

11 Claims, 5 Drawing Sheets

U.S. PATENT DOCUMENTS

| | | | |
|---|---|---|---|
| 3,833,406 A | | 9/1974 | White |
| 3,898,344 A | | 8/1975 | Masuoka et al. |
| 3,914,174 A | | 10/1975 | Fuchs |
| 4,036,360 A | | 7/1977 | Deffeyes |
| 4,081,397 A | | 3/1978 | Booe |
| 4,284,672 A | | 8/1981 | Stillman |
| 4,391,855 A | | 7/1983 | Geeck |
| 4,407,897 A | * | 10/1983 | Farrell et al. .................. 428/516 |
| 4,447,565 A | | 5/1984 | Lula et al. |
| 4,464,443 A | | 8/1984 | Farrell et al. |
| 4,485,204 A | | 11/1984 | Nabors |
| 4,547,536 A | | 10/1985 | Nabors |
| 4,646,914 A | | 3/1987 | Gipson |
| 4,730,726 A | | 3/1988 | Holzwarth |
| 4,770,944 A | | 9/1988 | Farrell et al. |
| 4,861,632 A | * | 8/1989 | Caggiano ..................... 428/35.2 |
| 4,929,482 A | | 5/1990 | Moritani et al. |
| 4,960,639 A | | 10/1990 | Oda et al. |
| 4,999,229 A | | 3/1991 | Moritani et al. |
| 5,078,909 A | | 1/1992 | Shigeta et al. |
| 5,153,038 A | | 10/1992 | Koyama et al. |
| 5,246,753 A | | 9/1993 | Koyama et al. |
| 5,322,161 A | | 6/1994 | Shichman et al. |
| 5,378,428 A | | 1/1995 | Inoue et al. |
| 5,393,457 A | | 2/1995 | Miksic et al. |
| 5,399,609 A | | 3/1995 | Moss |
| 5,431,970 A | | 7/1995 | Broun et al. |
| 5,500,041 A | | 3/1996 | Debuigne et al. |
| 5,529,177 A | | 6/1996 | Podd et al. |
| 5,633,054 A | | 5/1997 | Hollinger, Jr. |
| 5,686,161 A | | 11/1997 | Cullen et al. |
| 5,829,669 A | * | 11/1998 | Drummond et al. ........... 229/4.5 |
| 6,103,141 A | | 8/2000 | Incorvia et al. |
| 6,112,888 A | | 9/2000 | Sauro et al. |
| 6,135,273 A | | 10/2000 | Cuen |
| 6,214,426 B1 | | 4/2001 | Kawachi et al. |
| 6,279,736 B1 | | 8/2001 | Hekal |
| 6,451,423 B1 | | 9/2002 | Armat et al. |
| 6,531,197 B2 | | 3/2003 | Neteler |
| 6,534,571 B1 | | 3/2003 | Hoover |
| 6,562,452 B2 | | 5/2003 | Ferri |
| 6,991,095 B1 | | 1/2006 | Yamasoto et al. |
| 7,312,569 B2 | | 12/2007 | Kim et al. |
| 7,413,083 B2 | | 8/2008 | Belfance et al. |
| 2002/0006483 A1 | | 1/2002 | Neteler |
| 2002/0048552 A1 | | 4/2002 | Garrill et al. |
| 2002/0073530 A1 | | 6/2002 | Ferri |
| 2002/0090473 A1 | | 7/2002 | Lee et al. |
| 2003/0235664 A1 | | 12/2003 | Merical et al. |
| 2004/0023585 A1 | | 2/2004 | Carroll et al. |
| 2004/0170780 A1 | | 9/2004 | Giraud |
| 2004/0187438 A1 | * | 9/2004 | Clarke et al. ................... 53/400 |
| 2005/0140041 A1 | | 6/2005 | Seth |
| 2005/0140285 A1 | | 6/2005 | Park et al. |
| 2005/0255139 A1 | | 11/2005 | Hurd et al. |
| 2006/0077146 A1 | | 4/2006 | Palmateer |
| 2006/0138928 A1 | | 6/2006 | Kim et al. |
| 2006/0201620 A1 | | 9/2006 | Seo |
| 2006/0236868 A1 | | 10/2006 | Pansegrouw et al. |
| 2006/0258783 A1 | | 11/2006 | Rettenbacher |
| 2007/0084735 A1 | | 4/2007 | Lancesseur et al. |
| 2007/0135548 A1 | | 6/2007 | Seth |
| 2007/0269401 A1 | | 11/2007 | Portier |
| 2009/0022434 A1 | | 1/2009 | Chiba et al. |
| 2009/0071855 A1 | | 3/2009 | Bahuguna et al. |
| 2009/0223983 A1 | | 9/2009 | Leary |

FOREIGN PATENT DOCUMENTS

| | | |
|---|---|---|
| EP | 0 831 033 | 3/1998 |
| EP | 0 831 033 A | 3/1998 |
| EP | 0 879 772 B1 | 6/2002 |
| EP | 1 733 872 | 12/2006 |
| EP | 1 733 872 A | 12/2006 |
| GB | 1 069 929 A | 5/1967 |
| WO | 2004/080808 A | 9/2004 |
| WO | 2004080808 | 9/2004 |
| WO | 2006/115264 A | 11/2006 |

OTHER PUBLICATIONS

Supplementary European Search Report in related European Patent Application No. 03 76 1128, dated Jul. 3, 2008.

International Search Report in related International Patent Application No. PCT/US2008/052767, dated Jun. 19, 2008.

* cited by examiner

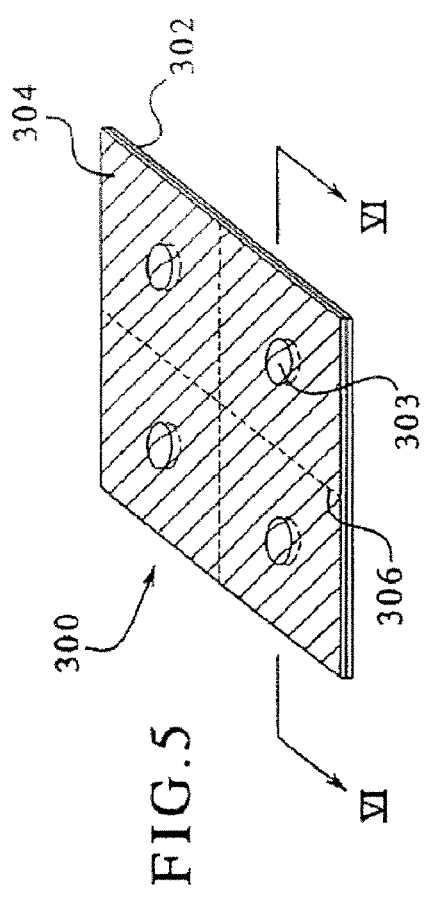
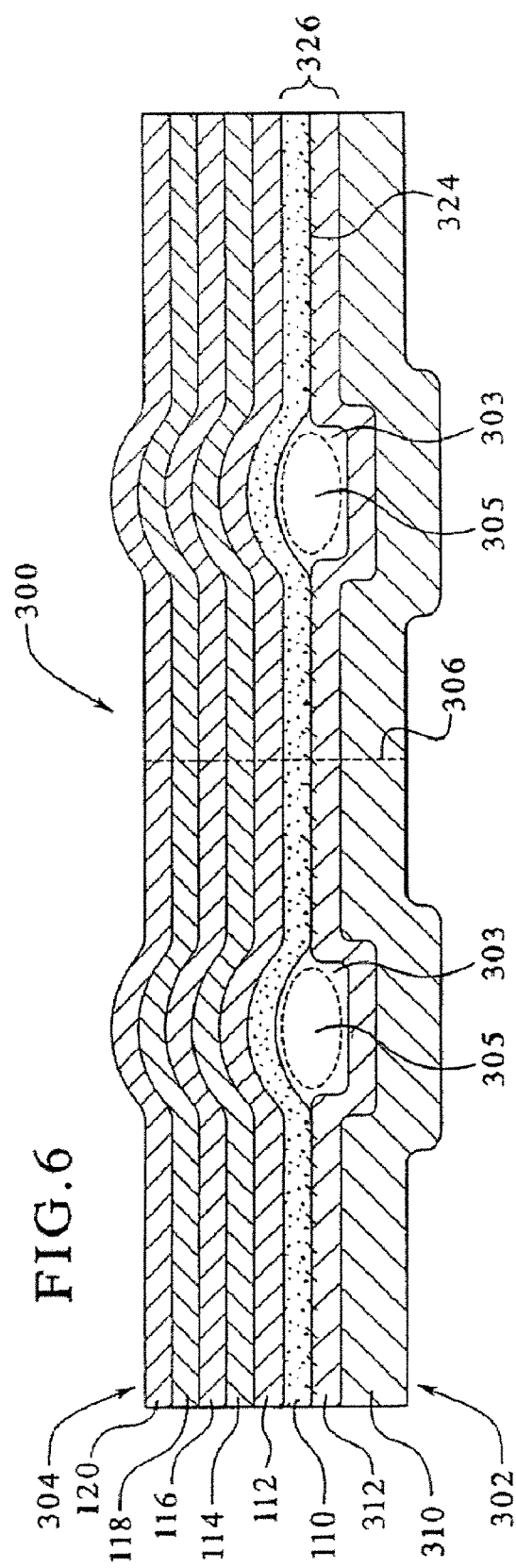

FILMS HAVING A DESICCANT MATERIAL INCORPORATED THEREIN AND METHODS OF USE AND MANUFACTURE

CROSS REFERENCE TO RELATED APPLICATIONS

This Application is a continuation-in-part of U.S. application Ser. No. 11/401,633 filed on Apr. 11, 2006, which is a continuation-in-part of U.S. application Ser. No. 10/385,131 filed on Mar. 10, 2003, which is a continuation-in-part of U.S. application Ser. No. 10/175,662 filed on Jun. 20, 2002. These applications are incorporated herein in their entirety.

FIELD OF THE INVENTION

Embodiments of the present invention relate to a film having a desiccant material incorporated therein. More specifically, embodiments of the present invention relate to a film structure having a desiccant material within a film layer of the film structure wherein said film structure is utilized in a package for a product that may be sensitive to the presence of moisture such as a drug coated medical stent or device. In addition, the embodiments of the present invention relate to methods of manufacturing and methods of using the film having a desiccant material incorporated therein.

BACKGROUND OF THE INVENTION

It is generally known to utilize plastic packaging to reduce exposure of products to atmospheric conditions, such as to moisture or oxygen, which may damage the products. For example, packaging for foodstuffs is well known, in that moisture and oxygen may cause the foodstuffs to become spoiled and inedible or otherwise undesirable. In addition, many products in the medical field, for example pharmaceutical products, nutraceutical products, and devices such as absorbable sutures, drug coated medical stents or other medical devices, may also be very sensitive to atmospheric moisture.

Typically, moisture-sensitive products may be encased in thermoplastic material that is relatively impermeable to water molecules. Specifically, many polymeric materials are utilized as barriers to moisture transmission. For example, a film of high density polyethylene (HDPE), or polyvinylidene chloride-methyl acrylate (PVdC-MA) copolymer may be utilized to restrict the movement of water molecules through the film. Oriented polypropylene, metallized oriented polypropylene, or metallized polyester would also be useful as moisture barrier material. In addition, metal foil is known to prevent the transmission of oxygen and/or moisture through polymeric packaging having a layer of metal foil contained therein.

Although these moisture barrier polymers may be useful in restricting the movement of moisture into a package, some moisture molecules can still make their way into the package to deleteriously affect the product contained therein. In addition, even when barrier materials are effective at restricting the transmission of water molecules through a package, certain features of the package may still allow for the transmission of water molecules. For example, where a barrier material is incorporated into a central layer of a film structure and the film structure is sealed to another film structure having a barrier material as a central layer, the edges of the package may not be protected by the barrier layers. This may allow moisture to make its way into a package along the edges of a heat sealed package.

One solution to maintaining a particularly low or virtually nonexistent level of moisture within a package is to incorporate sachets of desiccant material into the internal space of the package to remove the moisture from the headspace of the package. A sachet may effectively maintain a very low level of moisture in internal spaces of packages, but may have difficulty maintaining the same consistent moisture levels after the package has been opened and a product has been removed. For example, a typical package of moisture-sensitive products may contain a plurality of the products. A sachet of desiccant material incorporated into the package may only guarantee that moisture level of the package is maintained at a constant or minimal moisture level until the package is opened and the first product is thereby removed. The remaining products will be instantly exposed to atmospheric moisture when the seal of the package is broken. Although the sachet may remove some moisture from the headspace of the package after the package is opened, the remaining moisture-sensitive products, having already been exposed to moisture, may already be damaged. This may be especially true in bulk packaged materials where sachets are most often used. Desiccant materials are typically incorporated into liddings of jars or in sachets of multi-unit packages.

In addition, sachets of desiccant material may become saturated with atmospheric moisture relatively quickly thereby decreasing or eliminating their effectiveness. Moisture-sensitive products, therefore, stand a greater chance of being damaged by moisture in this case.

Moreover, the desiccant material contained in the sachets is typically in powder or granular form and may leak or otherwise spill from the sachets thereby contaminating the product or products contained within the package. For example, if the desiccant material contacts a food, pharmaceutical or nutraceutical product or medical device, the food, pharmaceutical or nutraceutical product or medical device may become contaminated with the desiccant material, which may be damaging to the health of an individual that consumes the food product or uses the medical device. In addition, spilled or broken desiccant sachet contents could create a deleterious effect on the efficacy of the medical device, such as a drug eluting stent (DES).

Additionally, although desiccant material is generally known to reduce the moisture content within a package, typical desiccant materials are "physical" desiccant materials, such as molecular sieves, that bind water molecules within pore spaces of a material. Typically, physical desiccant materials absorb water at all humidity levels, but will cease to absorb water when interstices of the physical desiccant material are filled. Therefore, physical desiccant materials may be ineffective at high humidity levels.

An additional type of desiccant material may be hydrate forming agents such as salts. Typical salts that may be utilized as desiccant material are sodium phosphate di-basic, potassium carbonate, magnesium chloride, calcium chloride, and calcium sulfate, although many others are known as well. Typically, the drying capacity is greatly influenced by the relative humidity within a package. Generally, no water is taken up by the hydrate-forming agent until the relative humidity reaches a value at which the first hydrate forms. In the case of calcium chloride, for example, the first hydrate occurs at less than about two percent relative humidity (RH). Water is then taken up by the hydrate forming salt until the first hydrate is completely formed by the salt. No further water is taken up by the salt until the relative humidity reaches a second level where the second hydrate forms. This process continues through as many hydrates as the agent forms at which point the substance begins to dissolve and a saturated solution is formed. The saturated solution will then continue to take up water.

Although these salts may be effective at removing water molecules from a quantity of gas that may be contained within the headspace of a package, since the salt only binds the water molecules within the salt, the water molecules may easily escape back into the package. This is known as breathing, and may cause deliquescence (water droplets and liquidization) inside the package. Typically, this can happen if the salt becomes saturated and if the temperature of the package increases, or if the pressure of the package decreases, which may occur during shipment or storage of the package.

In addition, salts may not allow moisture levels within a package to fall to a level that is necessary to protect the moisture-sensitive product that may be contained within the package. Typically, since salts have different levels of hydration, humidity levels may remain at certain level without decreasing until the level of hydration changes.

However, these salts may be utilized to maintain certain humidity levels within the headspace of a package. For example, certain products may require that a certain level of moisture or humidity be maintained within the package headspace. Headspace humidity control for products can be manipulated by incorporation of the appropriate hydrate forming agents.

The present invention may utilize chemical desiccant technology, which is more preferable because the moisture level within a package may be maintained at an extremely low level. Chemical desiccant materials chemically react with water molecules to form a new product, wherein the water molecules are chemically incorporated into the new product. For example, calcium oxide binds water in the following reaction:

$$CaO + H_2O \rightarrow Ca(OH)_2$$

Because the reaction noted above requires very high energy levels to reverse, it is, for all practical purposes, irreversible. Chemical desiccant materials typically absorb water at all humidity levels, and will continue to take up water at high relative humidity levels. These chemical desiccant materials, therefore, may reduce levels of moisture within the package headspace to zero or near zero, which is often desired to maintain maximum dryness of the product.

Examples of typical packages or products that would benefit from desiccant material are medical kits, such as home pregnancy test kits and medical instruments. In addition, other products include electrostatic shielding packaging for electronic parts, such as printer cartridges, circuit boards, televisions, DVDs, printers, modems, personal computers, and telecommunications equipment, etc. Further, other packaging that would benefit from desiccant material is packaging for foods, such as cheese, peanuts, coffee, tea, crackers, spices, flour, bread, etc. In addition, other products that would benefit from desiccant material incorporated into the packaging are shoes, boots, film products and cameras, and products that may be shipped by sea, such as high-value wood like mahogany that would be damaged if exposed to ambient humidity typically found in cargo ships.

A need, therefore, exists for polymeric plastic packaging that may be used in packaging to preserve products that may be sensitive to atmospheric moisture. The packaging may comprise films having a desiccant material incorporated directly into the film. In addition, films are needed that effectively control the level of moisture within packaging without using sachets or desiccant beads that may become ineffective over time, or that may contaminate products contained within the packaging. Moreover, films, methods of use and manufacture are needed to overcome the additional disadvantages as noted above with respect to sachets, beads or physical desiccants.

SUMMARY OF THE INVENTION

Aspects of the present invention relate to multilayer plastic polymeric flexible packaging films having a desiccant material incorporated within a layer of the film. More specifically, aspects of the present invention relate to a polymeric flexible film having a desiccant material incorporated within a layer of the film that is utilized as a package for a product that may be sensitive to the presence of moisture, such as a drug eluting medical stent. In addition, aspects of the present invention relate to methods of manufacturing and using the polymeric film having a desiccant material incorporated therein and methods of packaging, storing and/or increasing the shelf life and efficacy of a medical stent contained within a package comprised of the polymeric film.

It is, therefore, an advantage of aspects of the present invention, to provide a polymeric plastic packaging film having a desiccant material incorporated therein for packages that may contain moisture sensitive products. These products may be, for example, foodstuffs, medical devices, pharmaceutical and/or nutraceutical products and/or other products that may suffer from the deleterious effects of moisture. Specifically, medical devices that are useful in healthcare may be packaged using a film having a desiccant material contained within a layer of the film to maintain the utility of the devices. The desiccant material is utilized to control the moisture level within a package made by the film of the present invention.

In addition, it is an advantage of aspects of the present invention to provide a film having a desiccant material incorporated therein that would eliminate the need to incorporate into high cost and marginally effective sachets or beads of desiccant material that can contaminate products contained within packages if the sachets accidentally release the desiccant material into the package. Moreover, sachets or beads are typically higher in cost and may be relatively unsightly. Further, they may take up space within a package that could otherwise be used for product. If the desiccant materials within the sachets or beads are ingested, it may become a health hazard. By the present invention, the desiccant material is incorporated directly into the packaging film in a rigid solid state in the packaging film substrate.

Moreover, it is an advantage of aspects of the present invention to provide a film wherein the desiccant material is incorporated into the sealant layer of the film and wherein the film is easily extruded. In addition, many different types of desiccant materials may be utilized, thereby allowing for particular relative humidity levels within the packages.

Aspects of the present invention can further reduce packaging costs by allowing for the use of thinner and, therefore, less expensive barrier materials, such as aluminum foil, in some embodiments. For example, many flexible foil packages made using films of the present invention can have barrier layers having thicknesses that may be reduced by about 50% or more. Moisture can enter a package through a film structure where two film structures are heat-sealed together. Aspects of the present invention reduce the moisture absorption into the product by having the film absorb moisture entering the package at the end of the seal.

In addition, it is an advantage of aspects of the present invention to provide a film structure, and a package made therefrom, comprising a sealant film having a desiccant material and a peelable seal material that allows the film structure to be easily peeled from another film structure when the film structure is heat sealed to the other film structure. This allows moisture-sensitive products to be contained within a package and be protected from moisture while being easily openable. In addition, aspects of certain embodiments of the materials described herein can add the capacity for a moisture sensitive product to survive ETO (ethylene oxide gas) sterilization. ETO sterilization can require medical devices to be exposed for considerable periods of time, (for example, 24 hours), to vacuum, high humidity levels (for example approximately 90% relative humidity), and high temperatures (for example about 120° F.), which can be contrary to the normal operating parameters of a desiccant. Aspects of certain embodiments can provide a means to survive these abuse conditions and still maintain survivable moisture scavenging capability and capacity to protect the medical device. Aspects of certain embodiments can utilize a multilayer desiccant package including a layer of barrier material that creates a time-delayed effect and postpones the activation of the moisture scavenger. Aspects of certain embodiments can provide available desiccant in the package layers following the ETO sterilization cycle. This can allow for moisture scavenging to keep occurring and therefore assist in extending the shelf life of current medical devices such as drug eluting stents that presently may be damaged by excessive moisture left over in the package after ETO sterilization.

Additional features and advantages of the present invention are described in, and will be apparent from, the detailed description of the presently preferred embodiments and from the drawings.

DETAILED DESCRIPTION OF SEVERAL EMBODIMENTS OF THE INVENTION

Figure 1:
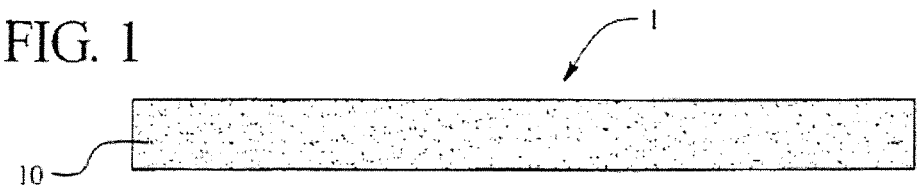
FIG. 1 illustrates a cross-section of a film comprising a desiccant material incorporated therein in an embodiment of the present invention.

The present invention relates to films, film structures, film systems, packages and methods of using and/or manufacturing the films, film structures, film systems and packages of the present invention. Specifically, the films may comprise a desiccant material incorporated into one or more of the films as an integrated component. More specifically, the desiccant material may be contained within one or more of the film layers in a film structure. For example the desiccant may be contained within a heat sealant layer of a film structure. As a further example, the desiccant may be contained with an interior layer of a film structure and not directly next to a pharmaceutical. The film structure may be utilized to produce a film system or package for a moisture-sensitive product wherein said film system or package has a first film structure in face-to-face contact with a second film structure and wherein said film structures are heat sealed together around the edges of the film system or package while the product is contained therein. Although many types of moisture-sensitive products may be contained within the packages made from the films or film structures of the present invention, the packages/film systems made therefrom are especially useful for packaging medical kits, instruments, and drug eluting and/or medical surgical stents.

One such product that could be packaged is a drug eluting stent. A stent is a medical device typically used to assist with blood flow. In one embodiment, a medical stent can be a tube-shaped metal scaffold inserted typically into the cardiovascular system to prevent artery collapse. The stent can be a solution to the issue of artery weakening resulting from angioplasty balloon dilation procedures.

A problem affecting about 30% of coronary arteries undergoing angioplasty is restenosis, which is the process of an artery becoming reblocked. In one embodiment of the present invention a bare metal stent is used. Bare metal cardiovascular stents can hold open weakened arteries, yet they lack full effectiveness at preventing restenosis. The presence of a stent also allows the direct introduction of pharmacologic agent, or drug, at the required site. An appropriate restenosis drug can be coated onto a stent, with the drug often embedded in a polymer layer for time-release capabilities. This kind of stent is known as a drug eluting stent, and its use has lowered the occurrence of restenosis from approximately 20-30% to below 10%. Two drug eluting stents have been approved by the FDA for sale in the United States since 2003 and 2004, and extensive research and testing of new drug eluting stents is currently underway. In addition, surgical stents may be used during dental surgery to guide in the placement of mandibular implants, for example. The employment of surgical stents increases the precision of dental implant surgery. Other pharmaceutical agents also can be coated onto drug eluting stents, such as paclitaxel and sirolimus, or other pharmaceuticals. Drug eluting stents can be extremely sensitive to moisture and oxygen. Excessive moisture may result in the drug eluting stent prematurely activating the drug coating prior to surgical placement in a body, resulting in a decreased amount of drug coating available on the stent at the time of insertion. Aspects of certain embodiments of the materials described herein may provide a solution to this problem of degradation of the drug coating on a drug eluting stent due to moisture remaining in the package and during processing before, during and after the ETO sterilization process.

Now referring to the drawings, wherein like numerals refer to like parts, FIG. 1 illustrates a film 1 of the present invention. The film 1 may be made from a polymeric material, such as a polyolefinic material. Preferably, the film may comprise polyethylene selected from the group consisting of ultra low density polyethylene, low density polyethylene, linear low density polyethylene, medium density polyethylene, and high density polyethylene, and may be made via any known method of making polyethylene, such as via Ziegler-Natta catalysts, or single-site catalysts, such as metallocene catalysts. Moreover, the film may preferably comprise ethylene copolymers, such as ethylene alpha-olefin copolymers, ethylene-methyl acrylate copolymer, ethylene vinyl acetate copolymer, and other like polymers. In addition, the film may comprise polypropylene homopolymer or copolymer, either alone or blended with polyethylene or polyethylene copolymers, as noted above. In addition, the film may comprise modified polymeric materials, such as modified via maleic anhydride, or other like modifiers for polymeric materials having particular characteristics. Specific materials that may be useful as the sealant layer include DuPont APPEEL® and BYNEL® or polybutene for peelseal.

The film 1 may further comprise a desiccant material 10 blended therein, such as any known desiccant material that may blend with polymeric resins that can be made into films. Specifically, desiccant materials that may be useful for the present invention include, but are not limited to calcium oxide, magnesium oxide, strontium oxide, aluminum oxide, partially hydrated aluminum oxide, sodium phosphate dibasic, potassium carbonate, magnesium chloride, calcium sulfate, molecular sieves, clays, or any other desiccant material useful for the present invention. In some embodiments of the invention chemical desiccant materials are preferred, such as calcium oxide, magnesium oxide and strontium oxide.

Chemical desiccant materials are preferred in some embodiments because chemical desiccant materials irreversibly bind water molecules within the crystalline product via a chemical reaction. The water molecules typically cannot be released into the package at higher temperatures or lower pressures. In addition, chemical desiccant materials may more effectively remove humidity from the headspace of a package made from the film 1.

Hydrate-forming salts may also be used, and may effectively maintain constant relative humidity levels within the headspace of a package made from the film 1. Specific levels of humidity may be maintained depending on the hydration levels or state of the hydrate-forming salt within the polymer material.

A preferred chemical desiccant material that is useful for the present invention is calcium oxide, which irreversibly forms calcium hydroxide via a chemical reaction.

The desiccant material can be incorporated into the film 1, in an embodiment, at a level of between about one weight percent and about 90 weight percent. In an embodiment, the desiccant material can be incorporated into the film 1 at a level of between about 20 weight percent and about 60 weight percent. In another embodiment, the desiccant material can be incorporated into the film 1 at a level of between approximately 10 weight percent and approximately 40 weight percent. In yet another embodiment, the desiccant material can be incorporated into the film 1 at a level of between approximately 20 weight percent and approximately 40 weight percent. In an additional embodiment, the desiccant material can be incorporated into the film 1 at a level of approximately 30 weight percent.

In an embodiment, the film 1 may comprise a quantity of a masterbatch of polymer and desiccant material. For example, the masterbatch may preferably comprise polyethylene having calcium oxide blended therein. Specifically, the masterbatch may comprise about 50 percent by weight polyethylene and about 50 percent by weight calcium oxide. The masterbatch can be further blended into another polymeric material, such as low density polyethylene, in a ratio of about 60 percent by weight masterbatch and 40 percent by weight low density polyethylene. Therefore, the film 1, in an embodiment, may have a desiccant material content of about 30 weight percent in the film 1. In additional embodiments, the masterbatch can be blended with a modified ethylene vinyl acetate copolymer or modified ethylene methyl acrylate copolymer, such as DuPont APPEEL® or polybutene resins, which can provide the sealant film structures with a peelable seal feature.

It should be noted that although the film 1 is illustrated as a single independent layer, film 1 may be incorporated into a multilayer structure such as via coextrusion with other film layers, extrusion or coextrusion coating, adhesive lamination, extrusion lamination or any other method of making multilayer film structures. In addition, the other films and layers mentioned herein may be single independent layers, or may be incorporated into a multilayer structure such as via coextrusion with other film layers, extrusion or coextrusion coating, adhesive lamination, extrusion lamination or any other method of making multilayer film structures. For purposes of packaging drug eluting stents a coextrusion is preferred, as a coextrusion can allow for the addition of a barrier layer to protect the desiccant in the moisture scavenging layer. The incorporation of a barrier layer may also be achieved by adding an adhesive or extrusion coating layer to an independent layer. An aspect of the current invention can involve the use of moisture scavenger desiccant in combination with a barrier layer to allow the moisture scavenger desiccant layer to survive the ETO sterilization cycle with remaining efficacy to protect the drug eluting stent from being exposed to excessive moisture. This protection from moisture can allow the drug eluting stent to have a greater shelf life and value to the users.

Figure 2:
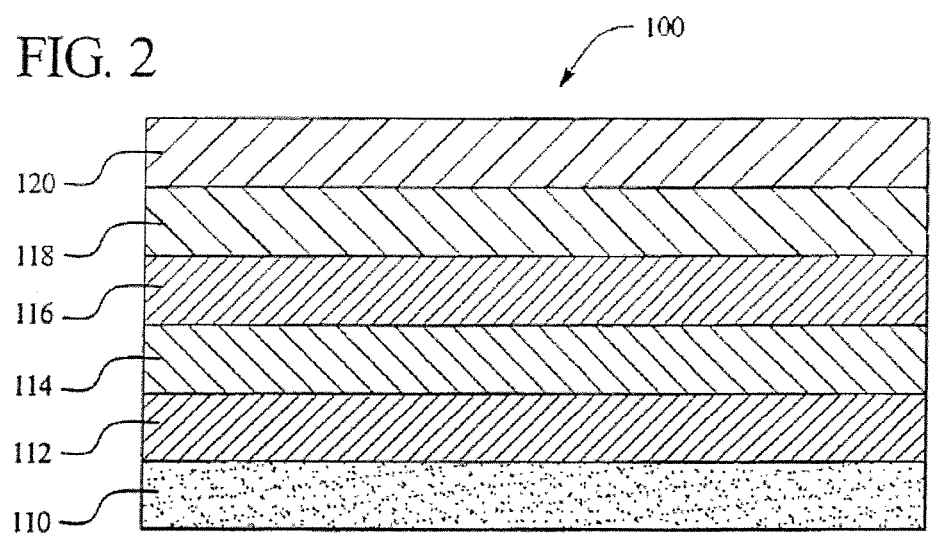
FIG. 2 illustrates a cross-sectional view of a film structure having a film layer comprising a desiccant material incorporated therein in another embodiment of aspects of the present invention.

FIG. 2 illustrates an embodiment of the invention, in which a film structure 100 of the present invention incorporates a film layer 110 having a desiccant material incorporated therein, as detailed above with relation to the film 1. Specifically, the film layer 110 may comprise a polyolefinic material, such as polyethylene, as described above, or polypropylene. Preferably, the polyolefinic material comprises polyethylene. The desiccant material may comprise a chemical, physical, or hydrate-forming desiccant material, although a chemical desiccant material is preferred.

In addition, the film layer 110 may be between about 1 mil and about 10 mils thick and may form a sealant layer or a product contacting layer in a package made from the film structure 100. In an embodiment, the film layer 110 may be between about 1 mil and 5 mils thick. In another embodiment, the film layer 110 can be between about 1.5 mils and about 3.5 mils thick.

The film layer 110 may further comprise a component that provides a peelable seal when used as a sealant layer that is heat sealed to another film structure or to itself. A resin blend that allows for a peelable seal is DuPont APPEEL®, which is either modified ethylene vinyl acetate copolymer or modified ethylene methyl acrylate copolymer, each of which is designed to provide a peelable seal when heat-sealed to other film layers, such as polyvinylchloride (PVC). Alternatively, a seal-poisoning component may be utilized, wherein a material, such as polybutylene, may be blended with the sealant resins to provide "poisoned seals" when sealant layers made from such resins are heat-sealed to other film layers, which can provide adequate sealing protection but can be easily separable using digital pull-apart forces. This is one preferred method drug eluting stent packaging. In addition, a desiccant material, such as calcium oxide (CaO) can be used as the peelable seal component, such that when heat-sealed to another film component, the film structure may be relatively easily separable using digital pull-apart forces.

Alternatively, the peelable seal component may not be present in the heat sealant layer, as described above, but may be present in a heat sealable layer of a second film structure that is heat-sealed to the film structure containing the desiccant material. This allows the peelable film component to be present in either the film structure containing the desiccant material or the second film structure that the film structure containing the desiccant material is heat-sealed to. In addition, the peelable seal component of the present invention may be contained within the first tie layer or adhesive layer of the film structure containing the desiccant material, or alternatively, to a tie layer or adhesive layer of the second film structure that the film structure containing the desiccant material is heat-sealed to. Therefore, it should be noted that the peelable film component can be contained within any layer or any film structure that allows the film structure containing the desiccant material to be pulled from the second film structure with digital pull-apart forces, while maintaining protection from moisture prior to pulling the film structures apart.

In an embodiment, the remaining film layers of a film structure of the present invention may be any material that may be utilized to form a package with the film layer 110 as a sealant layer or a product contacting layer. Moreover, any number of layers may be incorporated into the film structure 100 as may be needed to form a package having desired characteristics. An embodiment of the film structure of the present invention includes the heat sealant layer 110 as noted above. The heat sealant layer 110 may be adhered to a barrier layer 114 by a tie or adhesive layer 112. In addition, the film structure may comprise an outer layer adhered to said barrier layer via a second tie or adhesive layer disposed between said outer layer and said barrier layer. Finally, the film structure of the present invention may comprise a primer layer or printed layer disposed between said outer layer and said tie adhesive layer.

In an embodiment, a tie or adhesive layer may be a coextrusion of low density polyethylene (LDPE) and ethylene acrylic acid copolymer (EAA), wherein said LDPE is disposed adjacent to the sealant layer and the EAA is disposed adjacent to the barrier layer, as described below, although other polymeric materials may be utilized that adhere the heat sealant layer to the barrier layer. In an embodiment, the tie or adhesive layer is a non-aqueous adhesive. In some embodiments of the invention, use of a non-aqueous adhesive may assist with diminishing the amount of water or moisture in the headspace within a package. The barrier layer may be made of a polyvinylidene chloride-methyl acrylate copolymer, Honeywell ACLAR® (a high density fluorocarbon polymer), metal foil, such as aluminum foil, cyclo-olefin copolymer (COC), a blend of COC and high density polyethylene, nylon, high density polyethylene, polypropylene, such as oriented polypropylene and metallized oriented polypropylene, metallized polyester, or blends of these materials. In an embodiment, the barrier layer may be approximately 70-90% by weight COC and approximately 10-30% by weight HDPE. In another embodiment, the barrier layer may be approximately 80% by weight COC and approximately 20% by weight HDPE. Other percentages for blends of COC and HDPE also may be used. The barrier layer may be any thickness that may be necessary to reduce the transmission of water molecules through the film structure 100. In an embodiment, the barrier layer may be about 0.35 mils when the barrier layer is aluminum foil. In other embodiments, the barrier layer may have a thickness of approximately 75 microns or less, and may have a thickness of approximately 50 microns or less. In another embodiment, the barrier layer may have a thickness greater than 75 microns, including a thickness of 100 microns or more. Of course, the barrier layer may be other thicknesses depending on the barrier material that is utilized. The tie or adhesive layer may aid in binding the polyolefinic material of the heat sealant layer to metal foil that may be used as the barrier layer.

Tie or adhesive layer 116 may be a coextrusion of LDPE and EAA and may be similar, if not identical, to film layer 112, wherein the EAA is disposed adjacent to the barrier layer 114, and the LDPE is disposed adjacent to the film layer 118 or film layer 120, as described below. Film layer 118 may be a primer layer and/or a printed layer. If the film layer 118 is a printed ink or pigment layer, it may form a printed label or other printed indicia on the film structure 100. Finally, film layer 120 may be an outer abuse layer, and may comprise Honeywell ACLAR®, polyethylene terephthalate (PET), oriented polypropylene (OPP), polyethylene, nylon, foil, metallized substrates, or any other material apparent to one having ordinary skill in the art. Optionally, a secondary sealant layer (not shown) may be disposed adjacent to the sealant layer 110 and may protect the product from the desiccant material contained in the sealant layer 110. The optional secondary sealant layer may form the product contacting layer of the film structure 100 and may be about 0.5 mils or less. However, the secondary sealant layer may be any polymeric material that helps to protect the product from contacting the desiccant material.

As stated above, the barrier layer 114 may be a metal foil or Honeywell ACLAR® that may be any thickness (for example only, 25 microns, 50 microns, 100 microns) to reduce the transmission of moisture through the film. The number of pinholes present in a metal foil, for example, is inversely related to the foil thickness. Therefore, a thicker foil tends to have fewer pinholes. However, if the desiccant material of the present invention is in the heat sealant layer 110 thinner foil or ACLAR® can be utilized in packages made from the film structure 100.

Metal foil or ACLAR® can be utilized to provide an effective barrier against moisture transmission through a film structure. However, metal foil can be relatively expensive and difficult to process. Therefore, the desiccant sealant layer 110 is effective at reducing or eliminating the transmission of moisture that may pass through the pinhole imperfections in relatively thin metal foil. Desiccant films, therefore, add significant protection to the inside space of a package made from the film structure 100 in addition to the inherent barrier protection provided by metal foil. Barrier layers may be relatively thinner when a film structure incorporates a desiccant sealant layer into the film structure, thereby saving on cost. Moreover, barrier layers such as COC/HDPE blends may be used more often when desiccant films are used.

Figure 3:
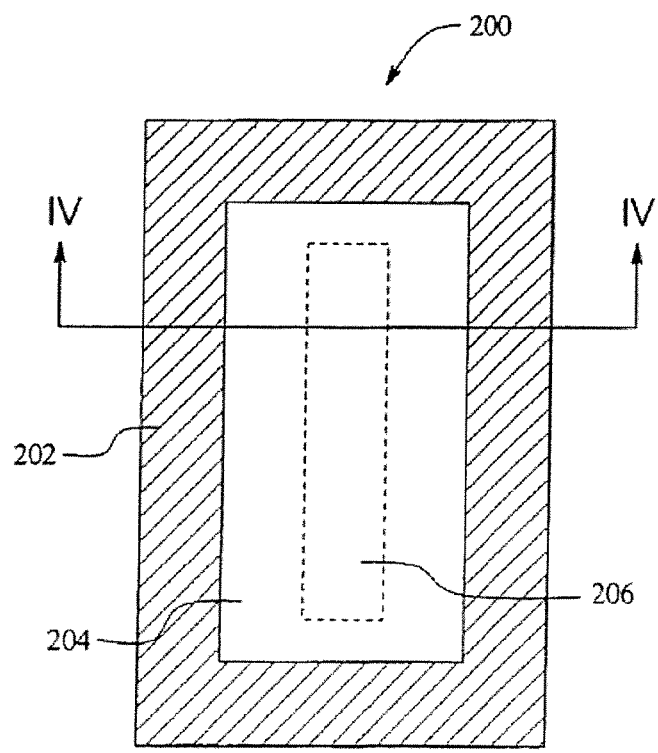
FIG. 3 illustrates a perspective view of a package made by the film structure in an alternate embodiment of aspects of the present invention.

FIG. 3 illustrates a package 200 made from a film structure of an embodiment of the present invention. Specifically, the package 200 is made from the film structure 100, as illustrated with respect to FIG. 2, described above. Specifically, the package 200 may comprise two film structures that are heat sealed together via a heat seal 202 that is formed around a perimeter of the package 200. Alternatively, the package 200 may comprise a single film structure that is folded and heat sealed around the perimeter of the package 200. The package 200 may further comprise a space 204 to contain a product 206. The product 206 may be sensitive to moisture, so that a desiccant material contained within the film structure or film structures reduces or eliminates the amount of water molecules within the space 204. A preferable product contained within the package 200 may be a kit useful in the medical field. A single instrument may be contained within the package 200 so that when opened and the instrument is removed, there are no other instruments within the package 200 to be contaminated by moisture.

Figure 4:
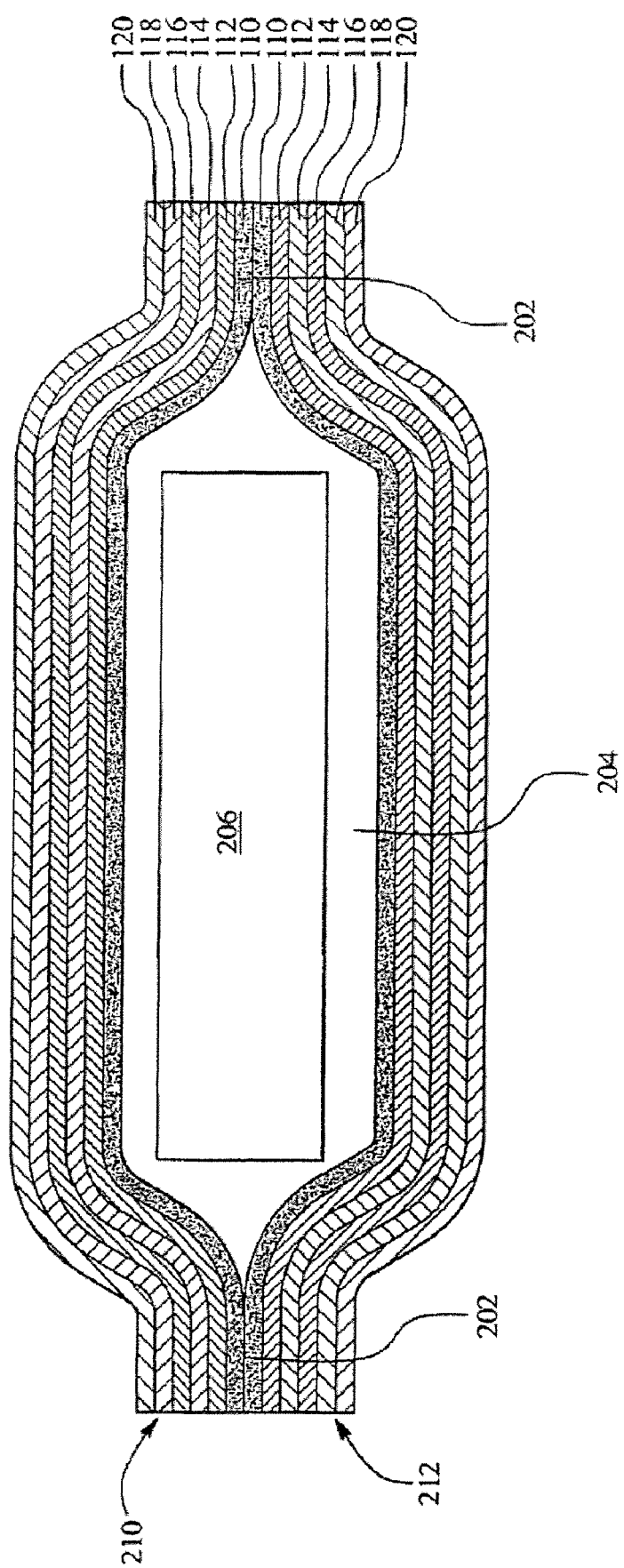
FIG. 4 illustrates a cross-sectional view of the package along line IV-IV, in the alternate embodiment of aspects of the present invention.
Figure 7:
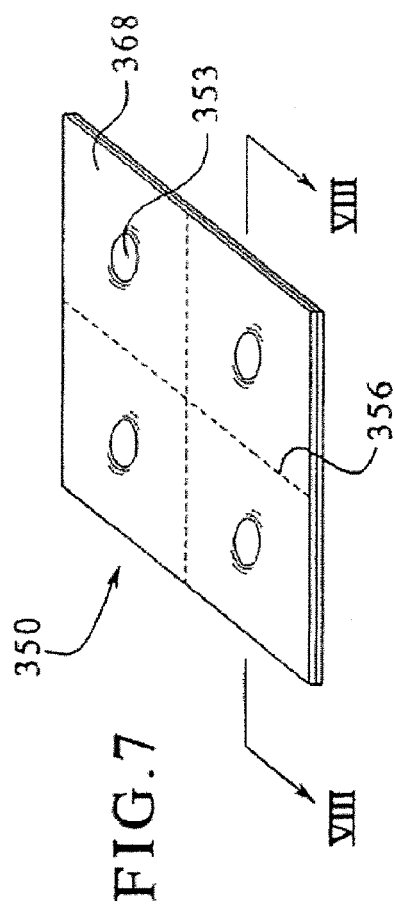
Figure 8:
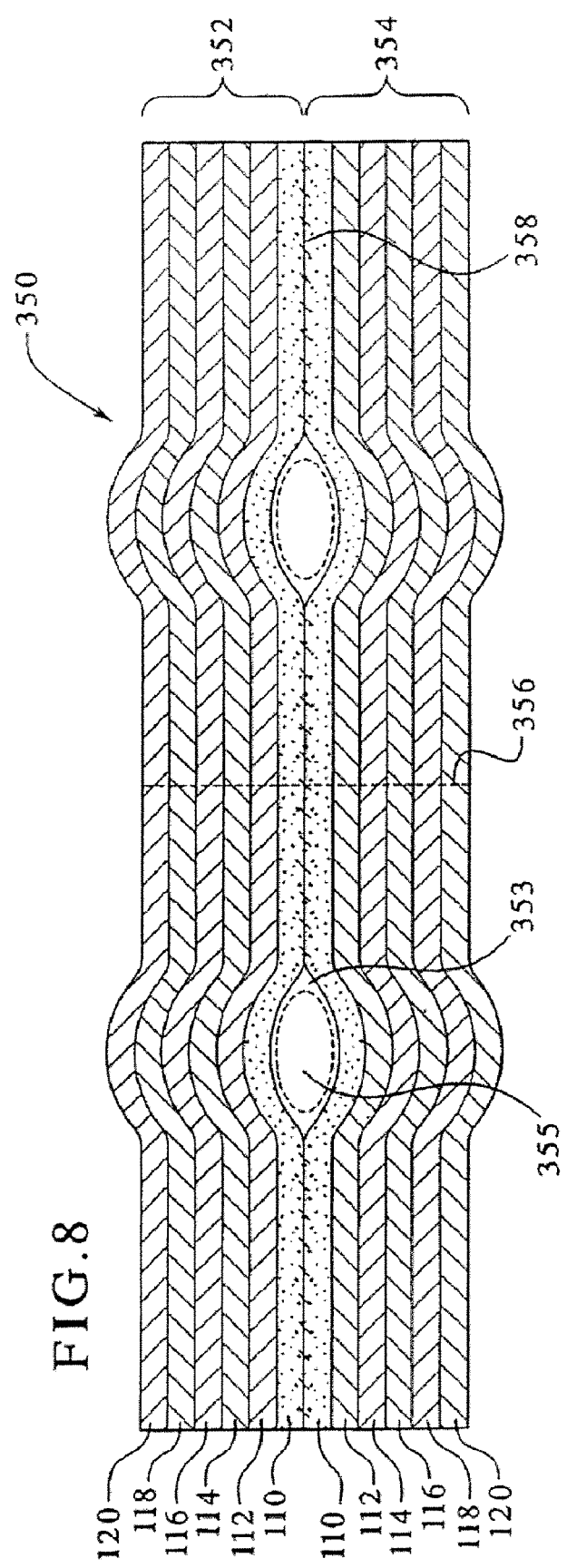
Figure 9:
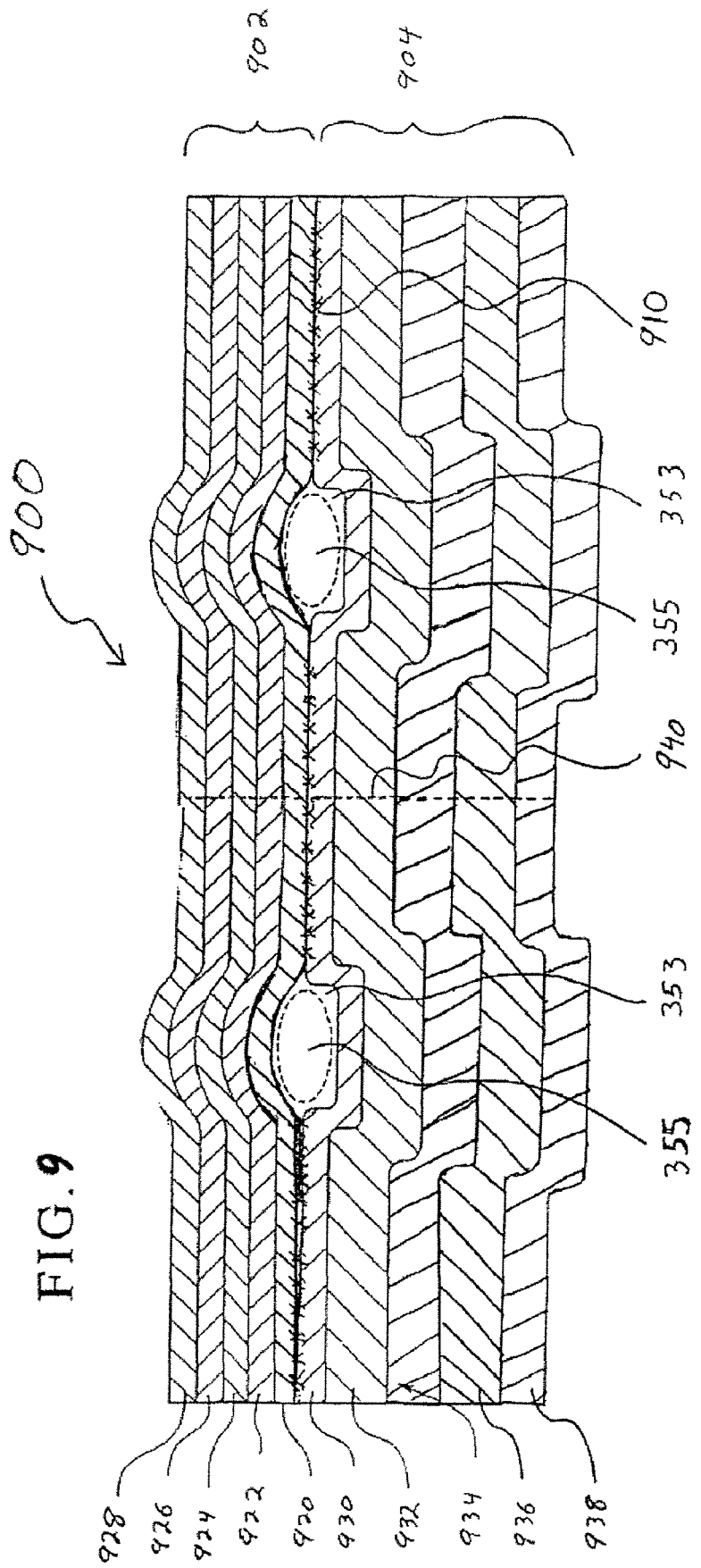

FIG. 4 illustrates a cross-section of the package 200 along line IV-IV, in an embodiment of the present invention. The cross-section shows two film structures 210, 212 that are heat sealed together at heat seals 202. The two film structures may be identical, and may comprise the same film layers as described above with respect to film structure 100. Specifically, the two film structure 210, 212 may comprise a plurality of layers: a sealant layer 110 of a polyolefinic material and a desiccant material; a tie or adhesive layer 112, comprising, for example, a blend of low density polyethylene and ethylene acrylic acid copolymer; a barrier layer 114 comprising, for example, a foil, ACLAR®. or metallized material; a tie or adhesive layer 116 comprising, for example, a blend of low density polyethylene and ethylene acrylic acid copolymer; a printed or primer layer 118; and an outer or abuse layer 120 comprising, for example, PET. The product 206, such as a medical instrument, is contained within the package 200 in the space 204.

While foil can reduce or effectively eliminate water transmission through film structures 210, 212 of the package 200, it cannot completely eliminate the transmission of moisture through the edges of the film structure. For example, FIG. 4 illustrates the cross-section of the package 200 along line IV-IV. As shown, the metal foil layer 114 of each film structure 210 and 212 are displaced from the portions of the film structure 210 and 212 that are heat sealed together. Therefore, there is an area 214 that is not protected by the metal foil layer 114 that may transmit water molecules into the space 204. If the desiccant material is incorporated into the heat sealant layer 110, then the desiccant material may effectively block moisture from passing into the interior space 204 of the package 200 thereby protecting the moisture-sensitive product contained therein. In addition, if the desiccant material is in the heat sealant layer that contacts a moisture-sensitive product or other contacts the interior space 204, the desiccant material can remove moisture molecules that may be contained within the interior space 204. The desiccant material also can remove moisture molecules when it is in a layer further away from the moisture-sensitive product.

In an additional embodiment, several films and/or layers may be used in combination to form multiple film structures of a film system. One film layer that can be incorporated into a film structure is a layer containing a desiccant. The desiccant layer can include a chemical desiccant that can act as a moisture scavenger. Examples of chemical desiccants include calcium oxide, magnesium oxide, strontium oxide, aluminum oxide or other chemical desiccants. The chemical desiccant can be combined with a polymeric material to form a film. Polymeric materials that can be used include polyethylene, linear low density polyethylene, COC and other polymeric materials. In an embodiment, the desiccant film layer can include approximately 20-40% by weight desiccant and approximately 60-80% by weight polymer. In another embodiment, the desiccant layer can include approximately 10-40% by weight desiccant and approximately 60-90% by weight polymer. In another embodiment, the desiccant layer can include approximately 10-50% by weight desiccant and approximately 50-90% by weight polymer. Depending on the desired capacity of the film system to scavenge moisture, more or less desiccant can be incorporated into the desiccant layer as well as the other layers of the film structures. In one embodiment, a desiccant film layer can have a thickness of approximately 4-8 mils. In some embodiments, a desiccant film layer can have a thickness of approximately 5-7 mils or approximately 6 mils.

In other embodiments, molecular sieve desiccants can be incorporated into a desiccant film layer. In one embodiment, the molecular sieve desiccant is a crystalline alumino-silicate. In some embodiments, the molecular sieve desiccant can have a pore size of no more than approximately 3, 4 or 5 angstroms. Molecular sieve desiccants may act more rapidly than many chemical desiccants. Thus, molecular sieve desiccants may take up water or moisture in a relatively quick manner. Molecular sieve desiccants may then reach their capacity to hold water. Many chemical desiccants, on the other hand, have a larger capacity to hold moisture or water than molecular sieve desiccants. Many chemical desiccants work more slowly at absorbing water or moisture than molecular sieve desiccants. However, many chemical desiccants will continue to absorb water longer than and will absorb more moisture than molecular sieve desiccants.

The film structure also may include a product contact layer. The product contact layer may be comprised of a substance that has been deemed acceptable to be in contact with a product such as a pharmaceutical. In one embodiment, the product contact layer can include polyvinylchloride (PVC). In another embodiment, the product contact layer can include COC, HDPE or a blend of COC and HDPE. Blends of COC and HDPE in some embodiments can be approximately 70-90% COC and approximately 10-30% HDPE or approximately 80% COC and approximately 20% HDPE. The product contact layer can have a thickness of approximately 62 microns or less in one embodiment, approximately 50 microns or less in another embodiment and approximately 100 microns, 200 microns or more in other embodiments.

The film structure also can include a barrier layer. The barrier layer can serve to limit the amount of moisture that can pass through the film structure. In some embodiments, the barrier layer can include one or more of the following substances: polyvinylidene chloridemethyl acrylate copolymer, high density fluorocarbon polymer, cyclo-olefin copolymer, metal foil, nylon, high density polyethylene, oriented or cast polypropylene, metallized oriented polypropylene, and/or metallized polyester. In one embodiment, the thickness of the barrier layer is approximately 75 microns or less. In another embodiment the barrier layer has a thickness of approximately 62 microns or less. In an additional embodiment, the barrier layer has a thickness of approximately 50 microns or less. In another embodiment, the barrier layer has a thickness of approximately 25 microns or less. In an additional embodiment, the barrier layer can have a thickness of less than 10 microns, especially where foil is used as the barrier. In a further embodiment, the barrier layer can have a thickness of approximately 100 or 200 microns or more. The thickness of the barrier layers will depend on the purposes and design of the overall film system.

A first film structure can be created by combining a barrier layer, a desiccant layer and a product contact layer. These layers can be combined through the use of an adhesive. The layers also can be coextruded or combined in other methods known in the art. In one embodiment, the adhesive may be a non-aqueous adhesive. The adhesive can be ethylene acrylic acid copolymer in one embodiment.

In one embodiment, several film layers are laminated together. An adhesive can be applied on one side of a desiccant film layer. The adhesive and desiccant layer can then be put through a drying tunnel to evaporate all or the majority of the solvent contained in the adhesive. After the drying tunnel, the desiccant layer containing the adhesive can be adhered to a product contact layer that may include a polymeric material such as PVC. The adhesive in some circumstances can be referred to as an adhesive layer.

In an embodiment, the film structure containing the desiccant layer and the product contact layer can have an adhesive disposed on the side of the desiccant layer opposite the product contact layer. Like the adhesive mentioned above, this adhesive can be a non-aqueous adhesive. The film structure can then be passed through a drying tunnel. The side of the desiccant layer having the adhesive can then be placed in contact with and adhered to a barrier layer. The three layers described above, the product contact layer, the desiccant layer and the barrier layer, can form a film structure. In one embodiment, the process of combining the product contact layer, the desiccant layer and the barrier layer takes place as a continuous process.

In another aspect of the invention, two desiccants can be used in the same film structure. In one embodiment, a molecular sieve desiccant and a chemical desiccant can be used in conjunction with each other. In one embodiment, a molecular sieve desiccant film can be formed and a chemical desiccant film can be formed. The chemical desiccant film can contain both a chemical desiccant and a polymeric material. The molecular sieve desiccant film can contain both a molecular sieve desiccant and a polymeric material. The polymeric material for both desiccant films can be polyethylene or linear low density polyethylene or other suitable polymer. These two desiccant films can be joined together into a film structure through adhesion, coextrusion, lamination, heat sealing or other methods. Adhesion can be obtained through the use of a non-aqueous adhesive.

A film structure containing both the chemical desiccant film and the molecular sieve desiccant film can be used in manners similar to those described herein for a single desiccant film layer. The dual desiccant film structure can be used in place of a single desiccant film layer or can be used in addition to a single desiccant layer. The terms film structure, film and multilayer film are frequently used interchangeably and should be considered interchangeable where appropriate herein.

In another aspect of the invention, a single film can incorporate several different types of desiccant. In one embodiment, a film can incorporate a chemical desiccant and a molecular sieve desiccant. In an embodiment, the film can include approximately 5-35% by weight chemical desiccant, approximately 5-35% by weight molecular sieve desiccant and approximately 30-90% by weight polymeric materials such as polyethylene, linear low density polyethylene, COC or other polymeric materials In one aspect of the invention, it may be desired to store one or more layers or film structures that include a desiccant for later processing. In some cases, a desiccant film may be sent from one processing location to another location for the addition of a product contact layer and a barrier layer. In some cases, a film structure such as a structure including a desiccant layer, a barrier layer and a product contact layer may be shipped to a remote location for further processing. A film layer or film structure containing a desiccant can be wrapped in a barrier layer such as a foil or other barrier layer and stored. The wrapping with the barrier layer can place the barrier completely around the desiccant containing film or film structure, thereby greatly inhibiting the passage of water or moisture into the desiccant. In an embodiment, the film layer or film structure can be stored for up to 6 months without significant loss in the moisture scavenging capacity of the desiccant. In other embodiments, the film layer or film structure can be stored for up to 12 months, 18 months or more.

The film structures 100 may be made via cast coextrusion, extrusion coating and/or extrusion lamination, adhesive lamination, blown-film coextrusion or monolayer extrusion or any other film-making method generally known to those having ordinary skill in the art. In an embodiment, extrusion temperatures for blown films and cast films can be approximately 300°-550° Fahrenheit. In an embodiment, the desiccant heat sealant layer may be made by compounding the desiccant material into the polymeric resin, and extruding or coextruding via blown extrusion, cast extrusion, or extrusion lamination into a monolayer film or a multilayer film. The remainder of the film structures may be extrusion or adhesive laminated together with the monolayer film or multilayer film. The desiccant heat sealant layer can be laminated to the remainder of the film structure, including the barrier layer of the film structure.

As noted in the above paragraph, several methods exist for constructing an effective flexible or rigid package using the present invention. These methods include, but are not limited to:

1. Blown film monolayer extrusion or multilayer coextrusion of a desiccant film that is extrusion laminated to a barrier material. This method can be preferred in certain embodiments.

2. Blown film monolayer extrusion or multilayer coextrusion of a desiccant film that is adhesive laminated to a barrier material with the use of adhesives and/or primers to bond the desiccant film to the barrier layer.

3. Cast film monolayer extrusion or multilayer coextrusion of a desiccant film that is extrusion laminated to a barrier layer.

4. Cast film monolayer extrusion or multilayer coextrusion of a desiccant film that is adhesive laminated to barrier materials with the use of adhesives and/or primers to bond the desiccant film to the barrier layer.

5. Extrusion or coextrusion coating wherein the desiccant layer and/or an adhesive layer are extrusion or coextrusion coated directly onto the barrier layer.

Of course, any other methods of making films, film structures, film systems and packages of the present invention may be utilized as may be apparent to one having ordinary skill in the art. Moreover, although film structures having barrier materials incorporated therein as a barrier layer of the film structures may be preferred, other film structures such as those not having a barrier material or barrier layer may also be produced as apparent to one having ordinary skill in the art.

In addition, in an alternate embodiment of the present invention, the desiccant material may further be utilized to provide an indicator showing whether the desiccant material has reached its capacity. In addition, this may further provide an indication whether the package integrity has been compromised. Generally, desiccant materials become cloudy when they have absorbed water, especially when incorporated into films that are transparent. In addition, when the desiccant material absorbs moisture, the package becomes heavier, less transparent and more opaque. An image or a message may be provided in a film structure containing the desiccant material. When the image or message is obscured to a certain point, such as when the image or message cannot be viewed anymore because of the cloudiness of the package, an individual may know that the desiccant material has reached its capacity, or is close to reaching its capacity, thereby indicating that the package, and therefore the product, is relatively old, or the package has been compromised and moisture has entered the package. Alternatively, the package may contain a moisture indicator visible through at least a portion of the package, such as a window or the like, to form or change colors, thereby indicating the presence of excess moisture. In an embodiment, cobalt chloride can be used as a moisture indicator.

In addition, several desiccant film layers can be used in a single film structure. In one embodiment, a molecular sieve desiccant film layer and a chemical desiccant film layer may be used in a single film structure along with other layers such as a product contact layer, a barrier layer and adhesives.

An aspect of the invention involves use and processing of film products in environments with humidity. Certain current packaging operations, such as packaging for pharmaceutical and/or nutraceutical products, can take place in clean rooms under low humidity conditions. In some cases humidity during some current packaging process may be kept at levels of approximately 20% relative humidity (RH) or lower. Aspects of the current invention allow for packaging operations to take place in higher humidity environments.

In one embodiment of the invention, a film structure comprising a product contact layer, a desiccant layer and a barrier layer can be adhered to a second film structure comprising a product contact layer, a desiccant layer and a barrier layer. The film structures can be adhered through heat sealing, adhesives or other method of adhesion. After this adhesion step, the finished film system can be referred to as a package and a product, such as a drug eluting stent, can be placed in the package. Each step of the process of forming the film structures into a package, including the addition of the product, can take place at ambient humidity. In an embodiment, the various steps detailed above can be carried out in an environment having an RH of greater than approximately 50%. In another embodiment, the various steps can be carried out in an environment having an RH greater than approximately 70%. In a further embodiment, the various steps can be carried out in an environment having an RH that is greater than approximately 80%.

Due to the desiccant in the film, the relative humidity in the package interior cavity will rapidly decrease from the relative humidity of the packaging environment. In an embodiment, the relative humidity in the cavity may be more than approximately 50% immediately or shortly after the packing process is complete. Due to the desiccant in the film, the relative humidity in the cavity may decrease to less than approximately 20% after approximately 36 hours after the packaging process is complete. In another aspect of the invention, the relative humidity may decrease to a relative humidity of less than approximately 10% 36 hours after the packaging process is complete. In further embodiments, the decrease in relative humidity will occur where the initial relative humidity of the cavity is higher than approximately 50%. In an embodiment, the initial relative humidity of the cavity may be more than approximately 70%, more than approximately 80% or more than approximately 90%, and the relative humidity of the cavity in an embodiment will be less than approximately 20% 36 hours later and in another embodiment will be less than approximately 10% 36 hours later. The relative humidity in the cavity will remain at a level of less than approximately 20% (in one embodiment) or less than approximately 10% (in another embodiment) for a period of more than 6 months (in an embodiment) and for a period of more than 12 months (in an embodiment).

By keeping the relative humidity of the headspace in the cavity low, the shelf life of the drug eluting stent, medical device, pharmaceutical or nutraceutical products can be increased. The shelf life of a pharmaceutical or nutraceutical product in a package containing a desiccant film described above will be more than approximately 1 year (in one embodiment), more than approximately 2 years (in another embodiment) or more than approximately 4 years (in another embodiment) as long as the integrity of the package is not compromised. The current shelf life of some drug eluting stents can be limited to about 60-90 days, which is an economic burden that results in a high cost factor associated with drug eluting stents. An aspect of the invention, wherein a drug eluting stent is stored in a desiccant package as described herein, provides an increased shelf life of more than about 6 months in an embodiment. In other embodiments the shelf life of a drug eluting stent in desiccant packaging may be more than 1 year. In an additional embodiment, the shelf life is greater than 2 years.

As with all materials to be used during surgery, stents must be sterilized. The most common sterilization method for stents is ethylene oxide (ETO) gas sterilization, because it can be gentle to the material being sterilized, yet kills microbial agents. In an embodiment, ETO sterilization involves exposure to a concentration of ETO of approximately 500-1000 mg/L in an atmosphere of approximately 90% (in one embodiment) relative humidity or at least 50% relative humidity (in another embodiment) or 30% humidity in an additional embodiment at a temperature of at least approximately 110° F. in one embodiment, at least approximately 115° F. in another embodiment and approximately 125° F. in a further embodiment. The exposure can take place for up to an hour in one embodiment, and up to ten, sixteen, or twenty-four hours in other embodiments. The exact conditions are variable. In an aspect of the invention, sterilization efforts of stents may be conducted at an ETO concentration between about 200 and 500 mg/L in an atmosphere of greater than 50% relative humidity and a temperature of about 125° F. for at least twelve hours. In another embodiment, sterilization of stents may be performed using at least 1400 mg/L ETO in an atmosphere of greater than 90% relative humidity at a temperature at or above approximately 115° F. for at least approximately one hour. The antimicrobial effectiveness of ETO increases proportionately with increased temperature, and sterilization time decreases as ETO concentration is raised.

At the conclusion of the sterilization, in an embodiment, the ETO gas is pumped out of the sterilization chamber. A moisture-sensitive product may be in a multilayer film package either open, or sealed through a vacuum vent, such as Tyvek® (DuPont), that allows the ETO gas to enter and exit the package. It is not practically possible to remove all of the moisture from the interior of the package via the suction. Once the package is removed from the sterilization chamber, it can be sealed (such as through heat sealing) and any Tyvek® vacuum vent cut off.

A disadvantage of ETO sterilization is that it introduces humidity to a moisture-sensitive product. The current shelf life of a sterilized drug eluting stent can be about two to three months, mainly due to degradation of the drug by moisture inside the package. There are two sources of this moisture, the first being the ETO sterilization atmosphere and the second being ambient moisture diffusing through the sealed stent packaging. To extend the drug eluting stent shelf life, these sources of moisture can be addressed.

In one aspect of the invention a package is used for storage of a moisture-sensitive product following sterilization via ETO gas of the moisture-sensitive product within the package. The package, in an embodiment, can be similar to the packages described herein. The package can be similar to the package shown in FIGS. 3 and 4 in an embodiment. The package can comprise a multilayer film comprising a first polymeric product contact layer, a first desiccant layer, a second desiccant layer, a first barrier layer, and a first laminating layer. The thickness of the polymeric product contact layer can depend on the permeation rate of the particular polymer employed. According to the multilayer films herein, the desiccant layers may each comprise a desiccant, such as calcium oxide or molecular sieves, blended with an extrudable olefin. Advantageously, in one embodiment, minimal or no moisture will diffuse through the product contact layer to the first desiccant layer during the time of the sterilization process, where it would consume the desiccant. On the other hand, in an embodiment, the moisture will be able to diffuse through the product contact layer following sterilization to promptly lower the relative humidity of the interior of the package and protect the product from degradation while it is in storage.

In one aspect of the invention, the second desiccant layer is located between the first desiccant layer and the barrier, for instance foil, layer. The second desiccant layer can absorb moisture that enters from the outside of the multilayer film package. It also can act as a backup desiccant in the event that the first desiccant layer becomes saturated. The first desiccant layer and the second desiccant layer may or may not comprise the same desiccant material. In one aspect of the invention, the first and second desiccant layers include chemical desiccants. In another aspect of the invention, one of the desiccant layers includes a molecular sieve desiccant and the other includes a chemical desiccant.

Another embodiment of the invention is a medical system including a moisture sensitive drug eluting stent and a desiccant package comprising two multilayer films, each of which include a first polymeric product contact layer, a first desiccant layer, a second desiccant layer, a first barrier layer, and a first laminating layer. The films are joined together through heat sealing or other process to form a package. In aspects of the invention, the desiccant package includes a plurality of desiccant layers, barrier layers, and/or laminating layers. Combining the ability to include any number of the various types of layers with a wide choice of layer thicknesses, the package is tailorable to different applications. In an embodiment of the invention, the desiccant package may be formed by folding one multilayer film into a type of pouch and sealing the edges. This provides a single space to contain the drug eluting stent, for example as illustrated in FIGS. 3-4, wherein element 204 refers to the space and product 206 refers to the stent.

An additional aspect of the invention is a method to sterilize a drug eluting stent by the ETO gas method. A drug eluting stent may be in a multilayer desiccant film package comprising a folded and sealed multilayer film including a product contact layer, two desiccant layers comprising desiccant materials that may or may not be the same, a barrier layer, and a laminating layer. In an embodiment, the package comprises two multilayer films as described herein. These two films, in an embodiment, can be heat sealed to each other near or at their perimeter. The desiccant film package may be sealed through a Tyvek® vacuum vent that allows the ETO gas to enter and exit the package. As described above, ETO sterilization of drug eluting stents involves the variables of ETO concentration, relative humidity, temperature, and exposure time. Each variable is operational over a range of chosen values, leading to a plurality of potentially effective conditions for sterilization. At the conclusion of the sterilization, the ETO gas is pumped out of the sterilization chamber. Once the package is removed from the sterilization chamber, it is sealed and the Tyvek® vacuum vent cut off. Regardless of the amount of humidity remaining in the sealed package at the completion of the sterilization process, the relative humidity in the package space at 36 hours after sterilization will be below approximately 20% in an embodiment. Providing that the desiccant package remains sealed, in aspects of the invention the relative humidity in the package space will be maintained below about 20% after at least 6 days, 6 months, 1 year, or 2 years in different embodiments.

EXAMPLES

The following examples are illustrative of preferred embodiments of the present invention, as described above, and are not meant to limit the invention in any way.

Example 1

The following Table 1 illustrates preferred materials and gauges for the film structure 100, as described above and illustrated with respect to FIG. 2.

TABLE 1

| Material | Gauge | |
|---|---|---|
| PET | 0.48 | mils |
| INK | 0.1 | #/ream |
| LDPE/EAA Coextrusion | 0.5 | mils |
| Foil | 0.35 | mils |
| LDPE/EAA blend | 0.5 | mils |
| LDPE/CaO blend | 1.5 | mils |

Example 2

The following Table 2 illustrates preferred materials and gauges for the film structure 100, as described above and illustrated with respect to FIG. 2, in an alternate embodiment of the present invention

TABLE 2

| Material | Gauge | |
|---|---|---|
| PET | 0.48 | mils |
| INK | 0.1 | #/ream |
| LDPE/EAA Coextrusion | 0.5 | mils |
| Foil | 0.35 | mils |
| LDPE/EAA blend | 0.5 | mils |
| LDPE/CaO blend | 2.5 | mils |

Example 3

Example 3 is a preferred embodiment of the package 200, described above and illustrated with respect to FIG. 3. The package may be made from film structures noted above, and preferably with respect to Examples 1 and/or 2. Specifically, the package 200 may be for medical instruments. Each package may be about 5.25 in. long and about 2.25 in. wide. The heat seals that are created around the perimeter of the packages are about 0.25 in. wide. Taking into consideration the heat seals, each package would have a total exposed internal surface of about 16.6 $in^2$.

Examples 4-6

The following table 3 illustrates preferred film structures and gauges for a sealant film layer that is extruded as a monolayer film or coextruded with a second layer, such as a tie or adhesive layer, and is then laminated to other film layers, such as a barrier layer, another tie or adhesive layer, an optional printed or primer layer, and an abuse layer. Each of the sealant films is made via a blown extrusion method, although other methods are available, such as cast extrusion.

TABLE 3

| Example | Film Materials | Gauge |
|---|---|---|
| 4 | 39% DuPont Appeel 2044<br>60% Ampacet X101499 LLDPE of<br>60% by weight calcium oxide<br>1% Ampacet slip 7012125 | 2.0 mil |
| 5 | 49% DuPont Appeel 1184<br>50% Ampacet X101499 LLDPE of<br>60% by weight calcium oxide<br>1% Ampacet slip 7012125 | 2.0 mil |
| 6 | 59% DuPont Appeel 1181<br>40% Ampacet X101499 LLDPE of<br>60% by weight calcium oxide<br>1% Ampacet slip 7012125 | 2.5 mil |

After the sealant films are made using blown extrusion, the films should be wrapped immediately with a moisture barrier material to avoid being contaminated by moisture in the atmosphere.

Example 7

Table 4 illustrates an embodiment of the present invention, whereby the sealant film layer, described above as Example 4, is laminated to other film layers to form a sealant film structure.

TABLE 4

| Film Layer | Materials | Gauge | |
|---|---|---|---|
| Inner heat sealant layer | Example 4, described above. | 2.0 | mils |
| First tie or adhesive layer | EAA/LDPE Coextrusion | 0.5 | mils |
| Barrier layer | Foil | 70 | gauge |
| Second tie or adhesive layer | EAA/LDPE Coextrusion | 0.5 | mils |
| Print layer | Ink | 0.1 | #/ream |
| Outer abuse layer | PET | 48 | gauge |

Example 8

Table 5 illustrates an embodiment of the present invention, whereby the sealant film layer, described above in Example 5, is laminated to other film layers to form a sealant film structure.

TABLE 5

| Film Layer | Materials | Gauge | |
|---|---|---|---|
| Inner heat sealant layer | Example 5, described above. | 2.0 | mils |
| First tie or adhesive layer | EAA/LDPE Coextrusion | 0.5 | mils |
| Barrier layer | Foil | 70 | gauge |
| Second tie or adhesive layer | EAA/LDPE Coextrusion | 0.5 | mils |
| Print layer | Ink | 0.1 | #/ream |
| Outer abuse layer | PET | 48 | gauge |

Example 9

Table 6 illustrates an embodiment of the present invention, whereby the sealant film layer, described above in Example 6, is laminated to other film layers to form a sealant film structure.

TABLE 6

| Film Layer | Materials | Gauge | |
|---|---|---|---|
| Inner heat sealant layer | Example 6, described above. | 2.5 | mils |
| First tie or adhesive layer | EAA/LDPE Coextrusion | 0.5 | mils |
| Barrier layer | Foil | 70 | gauge |
| Second tie or adhesive layer | EAA/LDPE Coextrusion | 0.5 | mils |
| Print layer | Ink | 0.1 | #/ream |
| Outer abuse layer | PET | 48 | gauge |

Example 11

Alternatively, each of the sealant film structures, described above with reference to Examples 7-9, can be heat-sealed to identical film structures to provide packages having spaces therein for moisture-sensitive products, such as pharmaceutical or nutraceutical products.

Example 12

Table 7 illustrates an alternative film structure that may be heat sealed to the sealant film structures described above with reference to Examples 7-9. The sealant film structures can be heat sealed to a base structure having a heat sealant layer comprising an amount of a desiccant material.

TABLE 7

| Film Layer | Materials | Gauge | |
|---|---|---|---|
| Inner heat sealant layer | Example 6, described above. | 2.5 | mils |
| Extrusion coating | APPEEL ® | 0.5 | mils |
| Forming layer | PVC | 6 | mils |
| Barrier layer | ACLAR ® | 1 | mil |

Alternatively, the forming layer of PVC and the barrier layer of ACLAR® may be switched. In addition, the extrusion coating layer of APPEEL® may be replaced with an adhesive layer such that the inner heat sealant layer may be adhesive laminated to the remainder of the film structure.

Example 15

In an embodiment of the invention, a medical system comprises a drug eluting stent packaged in a moisture-scavenging pouch in an environment of relative humidity greater than approximately 90%. A TAXUS™ (Boston Scientific, Natick, Mass.) paclitaxel-eluting stent is placed in a moisture-scavenging pouch comprising two multilayer films that are folded and sealed along three sides, comprising the materials listed in Table 8. The pouch can be envisioned as similar to the package 200 illustrated in FIG. 4. Table 8 includes the reference numbers corresponding to each layer, except for the print layer. The peelable HDPE layer is the product contact layer 110.

With the paclitaxel-eluting stent inside the moisture-scavenging pouch, the final side is sealed and the relative humidity inside the pouch initially can be at least 90% in an embodiment. Moisture diffuses through the peelable HDPE layer 110 and is quickly absorbed by the molecular sieve desiccant in the first moisture scavenging layer 112. At a time of 36 hours after the stent is sealed in the pouch, the relative humidity of the air surrounding the stent inside the pouch is less than about 20%. Calcium oxide is provided in the second moisture-scavenging layer 114 as a backup layer if the molecular sieves become saturated with moisture. The calcium oxide will also bind any water molecules that diffuse in from the ambient atmosphere through the pouch seal or the polyester abuse layer 120, the EAA/LDPE adhesive layer 118, and the foil barrier layer 116. After 3 months stored in ambient conditions, the relative humidity inside the pouch is less than approximately 20%. In addition, after 1 year and after 2 years, the relative humidity of the air surrounding the paclitaxel-eluting stent is less than about 20%. The stent is maintained in an environment that limits moisture-driven degradation of the paclitaxel, extending its shelf life to over two years.

TABLE 8

| Film Layer | Materials | Ref # | Gauge |
|---|---|---|---|
| Inner heat sealant layer | Peelable HPDE | 110 | 0.5 mils |
| First moisture scavenging layer | Molecular sieve/LDPE/ EAA Coextrusion | 112 | 1.5 mils |
| Second moisture scavenging layer | Calcium oxide/LDPE/ EAA Coextrusion | 114 | 1.5 mils |
| Barrier layer | Foil | 116 | 35 gauge |
| Tie or adhesive layer | EAA/LDPE Coextrusion | 118 | 0.5 mils |
| Print layer | Ink | Not shown | 0.1 #/ream |
| Outer abuse layer | Polyester | 120 | 48 gauge |

Example 16

An embodiment of the invention is a method to increase the sterilization of a drug eluting stent in a multilayer film package, such as the moisture-scavenging pouch of Example 15 described in Table 8. The method comprises exposure of the drug eluting stent, a sirolimus-eluting CYPHER™ stent (Cordis Corporation, Miami Lakes, Fla.), in an open pouch to a concentration of ETO of approximately at least 500 mg/L in an atmosphere of at least about 60% relative humidity at a temperature of approximately 125° F. for about an hour. The ETO gas is substantially evacuated and the moisture-scavenging pouch is then sealed, providing a relative humidity of the atmosphere around the drug eluting stent in the pouch of about 60% at a first time. Moisture diffuses through the peelable HDPE layer 110 and is quickly absorbed by the molecular sieve desiccant in the first moisture scavenging layer 112.

At a time of 36 hours after the sirolimus-eluting stent is sealed in the pouch, the relative humidity of the air surrounding the stent inside the pouch is less than about 20%. Calcium oxide is provided in the second moisture-scavenging layer 114 as a backup layer if the molecular sieves become saturated with water. The calcium oxide will also bind water molecules that diffuse in from the ambient atmosphere through the pouch seal or through the polyester abuse layer 120, the EAA/LDPE adhesive layer 118, and the foil barrier layer 116. After 6 months stored in ambient conditions, the relative humidity inside the pouch is less than approximately 20%. In addition, after 18 months and after 30 months, the relative humidity of the air surrounding the sirolimus-eluting stent is less than about 20%. This method results in both increased sterilization of the CYPHER™ stent by ETO gas in a humid environment and extended shelf life of the packaged stent due to the moisture-scavenging properties of the multilayer film package.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A medical system comprising:
a desiccant package comprising a multilayer film comprising:
a first moisture barrier layer;
a first product contact layer comprising a material selected from the group consisting of polyvinylchloride, cyclo-olefin copolymer, high density polyethylene or a blend of cyclo-olefin copolymer and high density polyethylene; and
a first desiccant layer disposed between the first moisture barrier layer and the first product contact layer;
wherein when the medical system is subjected for at least about one hour at a temperature of at least 110° Fahrenheit to an atmosphere comprising ethylene oxide and having a relative humidity of at least 30%, the first product contact layer allows the desiccant layer to survive the sterilization while retaining moisture scavenging efficacy of the desiccant layer, while allowing moisture to diffuse from the interior of the package and through the product contact layer after the package is sealed following ethylene oxide sterilization to lower the relative humidity of the interior of the package after the package is sealed and protect any product contained by the package from degradation by moisture present in the interior of the package while the sealed package is in storage, and
wherein the first desiccant layer comprises a chemical desiccant comprising one or more materials selected from the group consisting of calcium oxide, magnesium oxide, strontium oxide and aluminum oxide, and
wherein regardless of the amount of humidity in the interior of the package when the package is sealed following subjection to ethylene oxide sterilization, the relative humidity in the interior of the package is less than approximately 20% within a time period of less than approximately 36 hours after the desiccant package is sealed.

2. The system of claim 1 wherein when the first desiccant layer has the capacity to alter the relative humidity in the interior of the package after the package is sealed from approximately more than 50% when the desiccant package is sealed, to less than approximately 10% within a time period of less than approximately 36 hours after the desiccant package was sealed.

3. The system of claim 1 wherein after approximately 36 hours after the desiccant package was sealed the relative humidity within the sealed desiccant package remains less than approximately 20% for at least approximately 12 months.

4. The system of claim 1 wherein the first desiccant layer comprises approximately 20-40% by weight desiccant and approximately 60-80% by weight polymeric material.

5. The system of claim 1 wherein the first desiccant layer further comprises a molecular sieve desiccant.

6. The system of claim 5 wherein said the first desiccant layer comprises approximately 5-35% by weight chemical desiccant, approximately 5-35% by weight molecular sieve desiccant, and approximately 30-90% by weight polymeric material.

7. The system of claim 1 wherein the first desiccant layer comprises calcium oxide blended with an extrudable olefin.

8. The system of claim 1 wherein said first product contact layer comprises high density polyethylene (HDPE).

9. A medical system comprising:
a package comprising a first multilayer film structure and a second multilayer film structure wherein the package is formed by sealing the first multilayer film structure to the second multilayer film structure around the edges of the first and second multilayer film structures,
wherein the first multilayer film structure comprises
a first polymeric layer comprising a material selected from the group consisting of polyvinylchloride, cyclo-olefin copolymer, high density polyethylene or a blend of cyclo-olefin copolymer and high density polyethylene;

a first moisture barrier layer, and a first desiccant layer disposed between the first moisture barrier layer and the first polymeric layer, the first desiccant layer comprising a chemical desiccant comprising one or more materials selected from the group consisting of calcium oxide, magnesium oxide, strontium oxide and aluminum oxide; and wherein the second multilayer film structure comprises a second polymeric layer comprising a material selected from the group consisting of polyvinylchloride, cyclo-olefin copolymer, high density polyethylene or a blend of cyclo-olefin copolymer and high density polyethylene;

a second moisture barrier layer, and a second desiccant layer comprising a chemical desiccant, the second desiccant layer disposed between the second moisture barrier layer and the second polymeric layer;

wherein when the medical system is subjected to ethylene oxide sterilization conditions comprising an atmosphere comprising ethylene oxide and having a relative humidity of at least 30% at a temperature of at least 110° Fahrenheit for at least about one hour, the first polymeric layer allows the desiccant layer to survive the sterilization while retaining moisture scavenging efficacy of the desiccant layer, and allowing moisture to diffuse from the interior of the package and through the first polymeric layer after the package is sealed following ethylene oxide sterilization to lower the relative humidity of the interior of the package after the package is sealed and protect any product contained by the package from degradation by moisture present in the interior of the package while the sealed package is in storage, and wherein regardless of the amount of humidity within the package when the desiccant package is sealed following subjection to ethylene oxide sterilization, the relative humidity within the sealed package is less than approximately 20% approximately 36 hours after the desiccant package is sealed.

10. The system of claim 9 wherein, the first multilayer film structure further comprises a second desiccant layer.

11. The system of claim 9 wherein, when the relative humidity within the system is at least approximately 50% when the desiccant package is sealed following subjection to ethylene oxide sterilization, the relative humidity within the sealed package is less than approximately 10% approximately 36 hours after the desiccant package was sealed.

* * * * *